United States Patent [19]

Gutierrez

[11] 4,272,442
[45] Jun. 9, 1981

[54] CERTAIN TRICARBOXYLIC ACID DERIVATIVES

[75] Inventor: Eddie N. Gutierrez, Fort Lee, N.J.

[73] Assignee: Lever Brothers Company, New York, N.Y.

[21] Appl. No.: 104,637

[22] Filed: Dec. 17, 1979

Related U.S. Application Data

[62] Division of Ser. No. 970,827, Dec. 18, 1978, Pat. No. 4,226,781.

[51] Int. Cl.$^3$ ............................................. C07D 307/60
[52] U.S. Cl. ............................. 260/346.74; 260/465.4; 560/176
[58] Field of Search ..................... 260/346.74, 465.4; 560/176

[56] References Cited

U.S. PATENT DOCUMENTS 4,123,458  10/1978  Gutierrez et al. .................. 560/176

OTHER PUBLICATIONS

Huang et al., J. Chem. Soc. C., 1968 pp. 2217–2221.
Gelin et al., Bull. Soc. Chim France 1965 (1), pp. 139–143.

Primary Examiner—Henry R. Jiles
Assistant Examiner—Bernard Dentz
Attorney, Agent, or Firm—James J. Farrell; Melvin H. Kurtz; Irving N. Feit

[57] ABSTRACT

Novel polyfunctional compounds and a process for their preparation are disclosed. These compounds and their alkali metal salts are useful metal sequestrants and/or detergent builders. Selected compounds are also intermediates useful in the syntheses of aconitic acid as well as isocitric and alloisocitric acids and their lactones. The novel polyfunctional compounds are obtained from the reaction of maleic anhydride with selected active methylene or methine containing compounds.

4 Claims, No Drawings

CERTAIN TRICARBOXYLIC ACID DERIVATIVES

This is a divisional application Ser. No. 970,827 filed Dec. 18, 1978 now U.S. Pat. No. 4,226,781.

This invention broadly relates to novel polyfunctional compounds and a process for their preparation. The novel compounds may be converted into cis and trans aconitic acid and into a racemic mixture of isocitric acid, alloisocitric acid and the lactones of isocitric acid and alloisocitric acid. These compounds may also be saponified to form alkali metal salts corresponding to the particular compound employed. These salts, in turn, are metal sequestering agents and/or detergent builders. In the preferred embodiments the polyfunctional compounds are converted into either cis and trans aconitic acid or into a racemic mixture of isocitric acid, alloisocitric acid and the lactones of isocitric acid, alloisocitric acid as well as the lactones of cis and trans aconitic acid. These compounds are useful as food acidulants and metal ion sequestrants. The alkali metal, ammonium and substituted ammonium salts of isocitric acid, alloisocitric acid and cis and trans aconitic acid have utility both as metal ion sequestrants and detergent builders.

The reaction of active hydrogen compounds such as those containing methylene or methine moieties with unsaturated acid derivatives is known and is generally accomplished by means of the well known Michael reaction. This reaction is considered thoroughly in Chapter 3 of Volume 10 of the publication entitled "Organic Reactions" edited by John Wiley and Sons, Inc. In its original sense, as described in the publication, this reaction involves the addition of a donor moiety containing an alpha-hydrogen atom in a system

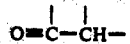

to a carbon-carbon double bond which forms part of a conjugated acceptor system of general formula

The addition proceeds under the influence of alkaline or basic catalysis.

Inherently in the Michael reaction, the donor moiety under the influence of the basic catalysis (sodium metal is a catalyst of choice) forms an anion which in turn reacts with the beta carbon of the acceptor system. Through the use of this reaction a series of compounds have been prepared. A listing of a large number of these reactions and reaction products appears on pages 271–544 of the above-mentioned publication. The reaction in certain selected instances does not require an added catalyst because one of the reactants contains its own basic function. The Michael reaction, thus, is extremely useful for the synthesis of selected compounds. However, difficulties arise in attempting to carry out the Michael reaction with acid anhydrides such as maleic anhydride. The sodium catalyst tends to react with the anhydride group, thus preventing the desired reaction from taking place. Use of typical Michael addition catalysts results in either no reaction or the wrong reaction taking place.

Berner, J. Chem. Soc. 1052 (1946) describes an uncatalyzed reaction between maleic anhydride and ethyl acetoacetate. Analysis of the product showed that a reaction had taken place between two molecules of maleic anhydride and one molecule of ethyl acetoacetate. Bird and Molton, Tetrahedron Letters No. 17, p. 1891 (1966) further describe this reaction product, and propose that a Michael addition is the first step of the reaction. This mechanism proposed by Bird, et al however was refuted by Berner and Kolsaker in Tetrahedron, Volume 24, p. 1199 (1968).

With reference to preparation of aconitic acid, and isocitric acid, alloisocitric acid and their lactones, prior art processes have been practically limited to natural fermentation. Although some synthetic methods have been proposed in the literature such as in the article by Michael, J. pr. Chem. 49 (ii), 21 (1894), Pucher and Vickery, J. Biol. Chem. 163 169–184 (1946) and Gawron et al., J.A.C.S. 80 5856–5860 (1958), none of these methods appear to have been commercialized.

U.S. application 642,850, filed Dec. 22, 1975, discloses a synthetic route for the preparation of aconitic acid, and isocitric and alloisocitric acids and their lactones, utilizing novel compounds produced by the uncatalyzed reaction of active hydrogen containing compounds with certain maleic acid ester salts. This process requires the conversion of maleic anhydride to an ester.

It can thus be seen that a catalyzed Michael reaction using maleic anhydride and a methylene or methine containing compound has not heretofore been accomplished. The prior art has not been able to prepare from these starting materials, polyfunctional compounds which may be reacted to form novel 5-member lactones, and further reacted to form isocitric acid and alloisocitric acid and their lactones.

Accordingly, an object of the present invention is to provide a process for producing novel polyfunctional compounds by adding an active methylene or an active methine compound across the double bond of maleic anhydride.

A further object is to produce a novel polyfunctional compound which may be converted into cis and trans aconitic acid or into a mixture of isocitric acid, alloisocitric acid and the lactones of isocitric acid and alloisocitric acid as well as salts of these acids.

Yet another object is to provide a novel method for preparing novel polyfunctional compounds which can be converted into metal ion sequestrants and detergent builders.

Other objects and advantages will appear as the description proceeds.

The attainment of the above objects is made possible by this invention which includes novel polyfunctional compounds and a process for their preparation. These novel compounds are anhydrides and acids having the general formulas:

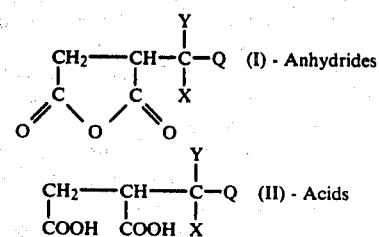

wherein:

X is COOR, CN or H and R is methyl or ethyl;

Y is COOR', CN, NO$_2$ or COCH$_3$ and R' is methyl or ethyl; and

Q is OH, H or CH$_3$.

Process For Preparing Novel Polyfunctional Anhydrides

The instant process involves a catalyzed reaction between maleic anhydride

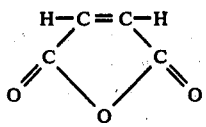

and an active methylene or methine containing compound of the formula:

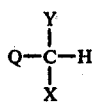     (III)

wherein X, Y and Q are as previously defined. The reaction which takes place is:

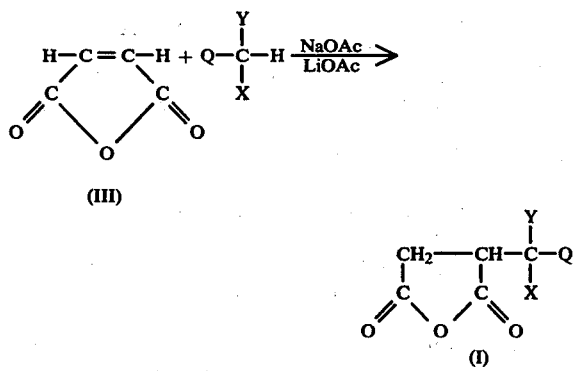

This reaction should take place under substantially anhydrous conditions.

An alkali metal acetate, such as sodium, potassium, or lithium acetate must be present as a catalyst; without the proper catalyst, the proper reaction products will not be obtained. Although lithium acetate does function as a catalyst, the presence of water of crystallization in this salt slows the reaction rate and requires the use of external heating. Examples of compounds which do not function as catalysts in this reaction are calcium acetate, sodium metal, pyridine, triethylamine and 1,4-diazabicyclo-(2,2,2) octane.

Examples of the methylene or methine containing compounds which react with maleic anhydride include diethyl and dimethyl malonate, diethyl methyl malonate, methyl cyanoacetate, nitroethane and dimethyl tartronate. Active methylene-containing compounds which do not react with maleic anhydride are phenylacetonitrile, phenyl methyl acetate, and higher (e.g. dibutyl) esters of malonic acid.

The preferred solvents for carrying out the above reaction are the active methylene or methine containing compounds themselves, due to the solubility of the acetate catalyst in these compounds. Other solvents which may be used include dioxane, tetrahydrofuran, tetrahydropyran, dimethoxyethane, diethoxyethane, dimethylsulfoxide, benzene and toluene. Solvents which react with maleic anhydride, such as hydroxylic solvents and dimethyl formamide, should be avoided. In cases where the catalyst is not highly soluble in the solvent, the reaction rate will be slower, and higher temperatures must be used.

The ratio of methylene or methine containing compounds to maleic anhydride must be at least about 1:1 to insure completion of the reaction, and may range as high as about 10:1 to obtain a reasonable solution viscosity. The preferred range is about 3:1 to about 5:1.

Reaction temperatures may range from about 25° C., to insure a reasonable reaction rate, to about 150° C. Too high a temperature results in excessive degradation of reactants and undesired side reactions. The preferred temperature range is about 50° C. to about 100° C. In some cases no external source of heat will be necessary due to the exothermic nature of the reaction; cooling, in fact, may be necessary.

The anhydride reaction product (I) hydrolyzes in water to give the diacid:

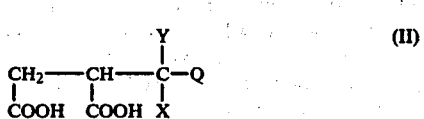     (II)

wherein X, Y and Q are as previously defined. Salts of compound (II) may be prepared by neutralization of the diacid.

These diacids and their alkali metal salts are useful as metal ion sequestrants and/or detergent builders. Selected diacids of the above formula also serve as intermediates useful in the preparation of aconitic acid, isocitric acid, alloisocitric acid, and the lactones of isocitric acid and alloisocitric acids.

Halogenation Of Selected Polyfunctional Compounds

Selected compounds of formula II having the formula

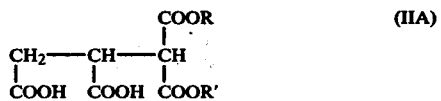     (IIA)

wherein R and R' are as previously defined may be halogenated with hypochlorous acid, hypobromous acid, sodium hypochlorite, sodium hypobromite and chlorine or bromine in aqueous solutions or mixed aqueous/methanolic solutions at pH's of about 2 to about 8 to produce compounds having the formula

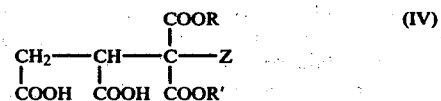     (IV)

wherein R and R' are as previously defined and Z is Br or Cl.

The halogenation process is preferably carried out in an aqueous reaction medium. The compound of formula IIA is introduced into a reaction vessel with water and, while stirring the mixture, a solution of a compound capable of generating HOZ (wherein Z=Cl or Br) is slowly added. The amount of reaction medium (i.e. water) used is not critical and is generally from about 50 to about 95% by weight of the total initial reaction mixture (i.e. compound IIA plus water). The HOZ required is conveniently generated from an alkali metal or alkaline earth metal hypohalite by acidification with a mineral acid solution such as hydrochloric or hydrobromic acid. Sodium hypochlorite or sodium hypobromite solutions are readily available as 5–15% solutions and are readily employed in this process. When the latter are used, the pH of the halogenation reaction mixture is controlled below about pH 8 and preferably between about 5 and about 7 by the simultaneous addition of a mineral acid. If bromine or chlorine is used in the halogenation reaction either directly or as bromine or chlorine water, the pH of the halogenation reaction mixture is maintained in the above range by the addition of alkali metal carbonates or hydroxides. The preferred pH range is utilized to maintain reasonable reaction rates.

The amount of HOZ required in the halogenation process is about 1 to about 1.1 moles per mole of the compound of formula IIA. If a substantially greater ratio of HOZ than 1.1 moles per mole of the compound of formula IIA is utilized, it will not affect formation of the product but is uneconomical. If substantially less than one mole is employed, the reaction will not proceed to completion.

The temperature of the halogenation process is usually in the range from about 0° to about 50° C. to avoid premature decarboxylation prior to halogenation of the compound and to avoid excessive loss of halogen which is in equilibrium with the hypohalous acid. Ambient temperatures are preferred as a matter of practicality and to keep side reactions to a minimum. After addition of the HOZ reactant is complete, the reaction is monitored by periodic sampling and analysis by NMR. The characteristic NMR frequency of the methylene protons will shift from high field in the case of the compound of formula IIA to a lower field as the halogenated compound of formula IV is formed in the reaction mixture. When the desired degree of halogenation is obtained, the compound of formula IV which is water soluble is isolated in its acid form by conventional methods involving acidification of the reaction mixture and recovery of the compound by, for example, extraction with a suitable organic solvent such as acetone.

Conversion of Selected Halogenated Polyfunctional Compounds Into A Mixture of Cis and Trans Aconitic Acid Under strongly alkaline conditions, the compounds of formula IV may be converted to a propene-1,1,2,3-tetracarboxylate, which upon acidification decarboxylates to form aconitic acid (cis and trans forms). The tetracarboxylate formation appears to proceed by means of a lactone intermediate (intramolecular lactonization) formed by the elimination of an alkaline earth metal halide. The lactone intermediate formula VI is converted to a hydroxy propane tetracarboxylate intermediate which, with elimination of water, forms the propene tetracarboxylate. The entire reaction scheme is exemplified as follows:

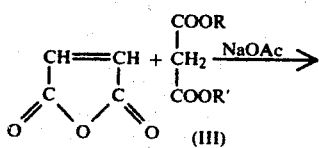

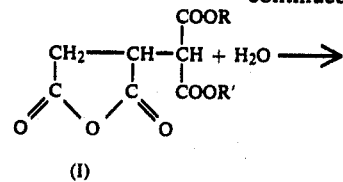

(I)

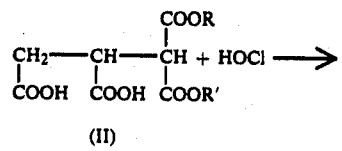

(II)

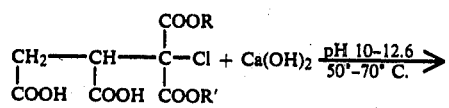

(IV)

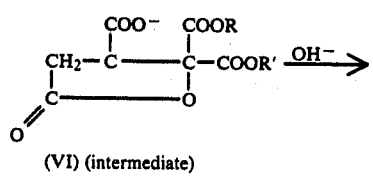

(VI) (intermediate)

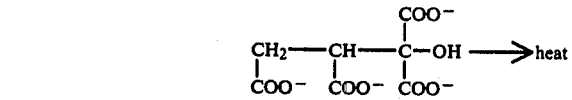

(Va) (hydroxy propane tetracarboxylate intermediate)

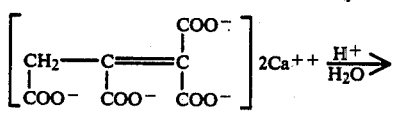

(V) propene tetracarboxylate

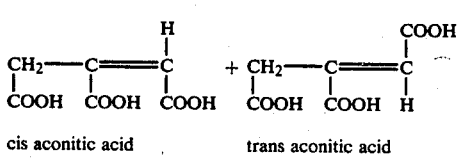

cis aconitic acid , trans aconitic acid

In the above reaction scheme, R and R' are independently methyl or ethyl.

In the practice of the above synthetic method, an aqueous solution of the formula IV compound is neutralized and made alkaline to a pH of about 10 to about 12.6, preferably from about 11 to about 12, by the slow addition of an alkaline earth metal hydroxide selected from the group Ca(OH)$_2$, Sr(OH)$_2$ and Ba(OH)$_2$, preferably Ca(OH)$_2$. The alkaline solution is heated at about 25° C. to about 100° C. preferably about 50° C. to about 70° C. until lactonization, saponification and dehydration are complete, i.e. about ½ hour to 2 hours. The reaction is preferably monitored by NMR. This is done by sampling the solution, treating with excess Na$_2$CO$_3$, filtering the insoluble calcium carbonate that forms, evaporating the filtrate and examining the residue by NMR. The reaction is stopped at maximum formation of the propeno-1,1,2,3-tetracarboxylate salt (V) by observing the intensity of the chemical shift for the methylene protons on carbon 3 at about 3.34δ. The tetracarboxylate calcium salt in the reaction mixture is then treated with dilute mineral acid to liberate the free acid which then undergoes decarboxylation to produce a mixture of cis and trans aconitic acids.

Conversion of Selected Halogenated Polyfunctional Compounds Into A Mixture of Cis and Trans Aconitic Acid, Isocitric Acid, Alloisocitric Acid and the Lactones of Isocitric Acid And Alloisocitric Acid In the case where $Sr(OH)_2$ is reacted with a compound of formula IV, a mixture of strontium salts of propene-1,1,2,3-tetracarboxylic acid and 1-hydroxypropane-1,1,2,3-tetracarboxylic acid may be formed, by following the reaction by NMR and stopping the reaction at the maximum formation of the propene-1,1,2,3-tetracarboxylate species (i.e. maximum intensity of the chemical shift for the methylene protons on carbon 3). On acidification with an aqueous solution of mineral acid, e.g. hydrochloric acid, or treatment with a cation exchange resin in its acid cycle, decarboxylation occurs to give a mixture of cis and trans aconitic acid, isocitric acid, alloisocitric acid and the lactones of isocitric acid and alloisocitric acid. The mixture of products may be isolated by conventional techniques such as solvent extraction or by evaporation of the water followed by extraction with a suitable solvent such as acetone and subsequent evaporation of the acetone extract.

In the case where $Ba(OH)_2$ is used to effect the intramolecular lactonization and saponification of the compounds of structure (IV) described above in the pH range 11-12, the reaction forms predominantly the 1-hydroxypropane-1,1,2,3-tetracarboxylate species as the barium salt. On acidification with an aqueous solution of a mineral acid, e.g. hydrochloric acid, or treatment with a cation exchange resin in the acid cycle, decarboxylation occurs to give a mixture of isocitric acid, alloisocitric acid and the lactones of isocitric acid and alloisocitric acid together with some cis and trans aconitic acid.

Conversion of Selected Halogenated Polyfunctional Compounds Into A Mixture of Isocitric Acid, Alloisocitric Acid and the Lactones Thereof In the special case where the compounds of structure (IV) are reacted with $Mg(OH)_2$ in aqueous mediumm, a pH of only about 8-10 is achievable. Under these conditions and between temperatures of about 25° C. and about 105° C. preferably from 90°-105° C., the reaction proceeds by means of intramolecular lactonization, saponification (with sufficient $Mg(OH)_2$) and decarboxylation to give a mixture of the magnesium salts of isocitric and alloisocitric acids. The latter salts may then be converted into the acid and lactone forms by either treatment with a suitable cation exchange resin or acidification with mineral acid and isolation by conventional techniques such as solvent extraction or evaporation of the water present followed by extraction of the residue with a solvent such as acetone and subsequent evaporation of the acetone extract.

Alternatively, the compounds of structure (IV) may be treated under weakly alkaline conditions of about pH 8-10 utilizing an aqueous solution containing the stoichiometric amount (one equivalent per mole of IV) of alkali metal hydroxide or carbonate or alkaline earth metal hydroxide at temperatures between 25° C. and 100° C. Under these conditions, intramolecular lactonization and saponification take place. A novel gamma/-lactone may be obtained by reducing the pH of the reaction solution to 1-3,

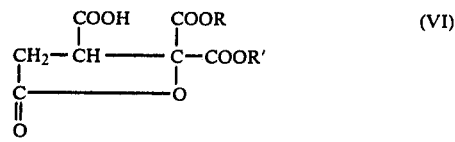

wherein R and R' are, as previously, independently methyl or ethyl. This novel lactone is more stable than the betalactone formed in accordance with U.S. patent application No. 642,850 filed Dec. 22, 1975, and assigned to the assignee hereof. In place of the alkali metal or alkaline earth metal hydroxides, a weak organic base such as pyridine or triethylamine may also be reacted with compounds of structure IV under anhydrous conditions to produce the same product (i.e. compound VI). Compound VI may be hydrolyzed to form isocitric acid, alloisocitric acid, and their lactones by heating in an acid solution.

In another embodiment, an aqueous solution of an alkali metal carbonate with or without an auxiliary organic base such as pyridine is reacted with a compound of formula IV to produce a compound of formula VII

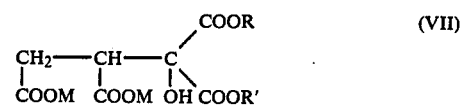

wherein R and R' are as previously defined and M is an alkali metal cation selected from the group lithium, sodium and potassium.

The compounds of structures (VI) and (VII) may be readily hydrolyzed by heating with the appropriate amount of aqueous solution of an alkali metal hydroxide, alkali metal carbonate or an alkaline earth metal hydroxide at a pH of about 9-11 and preferably about 9 to 10 to produce tetracarboxylate salts having the following structure:

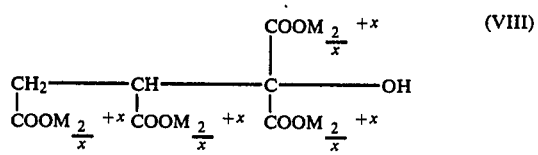

wherein $M_2$ is Li, Na or K or an alkaline earth metal cation selected from the group Ca, Sr and Ba and x is 1 or 2 and corresponds to the valence of the cation $M_2$.

The compounds of formula (VIII) wherein $M_2$ is Ca, Sr or Ba may also be treated with a solution of an alkali metal carbonate to produce the corresponding alkali metal salts (i.e. formula (VIII) wherein $M_2$ is Li, Na or K and x=1). The alkali metal salts of formula (VIII) are useful as detergent builders and metal ion sequestrants.

The compounds of formula (VIII) may each be converted into a mixture of isocitric acid, alloisocitric acid and the lactones of isocitric acid and alloisocitric acid by acidification with a dilute solution of a mineral acid such as hydrochloric acid, whereby decarboxylation occurs to produce said mixture of products.

In another preferred embodiment the halogenated species of formula (IV) may be heated with an aqueous solution of mineral acid, e.g. refluxing with 10% hydrochloric acid for about 1 to about 16 hours to simultaneously hydrolyze the ester groups, intramolecularly lactonize, and decarboxylate the compound to produce a mixture of isocitric acid, alloisocitric acid and the lactones thereof. The temperature of reaction is about 25° C. to about 110° C., preferably about 90° C. to 100° C. The reaction is run for a sufficient amount of time to result in the desired end product, usually about 6 hours to about 10 hours.

The reaction scheme thus is the same as that previously described for aconitic acid up to the product of formula (IV). The remaining sequence is as follows:

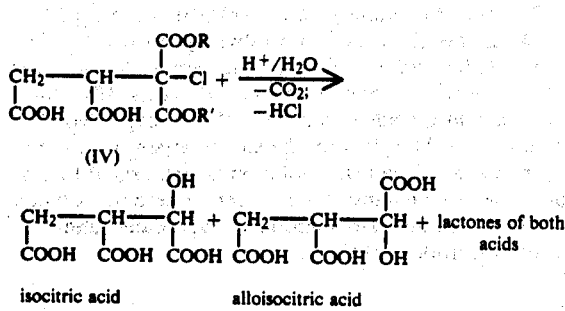

isocitric acid    alloisocitric acid

Thus in essence the invention consists of the described processes and compounds together with selected parameters as fully described herein. The following examples are designed to illustrate but not to limit the practice of the instant invention. Unless otherwise indicated, all evaporations are done with a roto evaporator and all percentages are by weight.

EXAMPLE 1
PREPARATION OF α-(DIMETHYLMALONYL)SUCCINIC ACID 50 grams of maleic anhydride (0.50 moles) are dissolved in 100 grams (0.76 moles) of dimethyl malonate and 12.5 g (0.14 moles) of sodium acetate is added. The reaction is maintained at 25° C. with external cooling and allowed to proceed overnight. 200 ml 1:1 ether:chloroform are added and the solution is filtered free of sodium acetate. The solution is then evaporated down to give a mixture of the dimethylmalonyl succinic anhydride and dimethyl malonate. The anhydride crystallizes out and is confirmed by NMR analysis.

NMR in CDCl₃

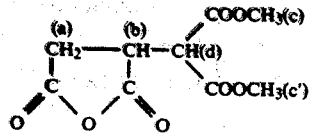

(a) CH₂ ABX multiplet at 3.00–3.22δ
(b) CH ABX multiplet at 3.4–3.7δ
(c)(c') CH₃ at 3.76 and 3.79δ
(d) CH doublet at 4.18δ
Melting point: 125.5° C.
IR: band at 5.38 for 5-membered anhydride.

One gram of the anhydride is dissolved in 10 ml water to give the acid, and is evaporated to dryness.

NMR in CDCl₃

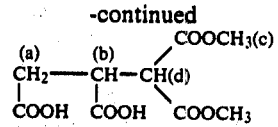

(a) CH₂ ABX doublet at 2.9–3.1δ
(b) CH ABX multiplet at 3.6–4.0δ
(c) CH₃ singlet at 4.0δ
(d) CH doublet centered at 4.29δ
Melting point. 92.2° C.

EXAMPLE 2
PREPARATION OF α-(DIMETHYLMALONYL)SUCCINIC ANHYDRIDE 20 grams (0.2 moles) maleic anhydride are dissolved in 50 grams (0.38 moles) dimethyl malonate. 2 grams (0.02 mole) potassium acetate are added and the solution is stirred and allowed to stand overnight. 100 ml ether are added and the solution is filtered. The filtrate is evaporated to give 18 grams of product.

EXAMPLE 3
PREPARATION OF α-(DIMETHYLMALONYL)SUCCINIC ACID

Example 1 is repeated using 1 gram (0.01 moles) lithium acetate as a catalyst, in place of sodium acetate, with 10 grams maleic anhydride and 16 grams dimethyl malonate. The reactants are heated to 75° C. for 8 hours, and the reaction product converted to the acid form.

EXAMPLE 4
PREPARATION OF α-(DIMETHYLMALONYL) SUCCINIC ACID 10 grams (0.1 mole) maleic anhydride and 13.2 grams dimethyl malonate are dissolved in 50 ml dioxane. Two grams sodium acetate are added and the solution is stirred for 1 hour. Since the reaction rate is negligible, the reactants are heated to 85°–90° C. for 6 hours, and then allowed to stand overnight. The solution is evaporated to dryness, the residue dissolved in 200 ml water, and the solution filtered. Upon evaporation of the solution to dryness, 14 grams (56.4% yield) of product are recovered.

EXAMPLE 5
PREPARATION OF α-(DIETHYLMALONYL)SUCCINIC ACID 20 grams (0.2 mole) maleic anhydride are dissolved in 42 grams (0.26 mole) diethyl malonate, and 5 grams (0.06 mole) sodium acetate are added. The temperature is maintained at 50° C. for one-half hour. 100 ml ether are added, and the solution is filtered and evaporated. The solution is extracted with petroleum ether to remove traces of diethyl malonate. 10.5 grams of anhydride are recovered and characterized by NMR.

NMR in CDCl₃

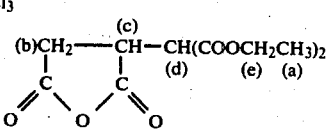

(a) CH₃ two triplets at 1.20–2.55δ

(b) CH ABX multiplet at 3.00–3.24δ
(c) CH ABX multiplet at 3.32–3.93δ
(d) CH doublet under the quartets (b)–(c)
(e) CH$_2$ 2 quartets at 4.0–4.5δ

Two grams of the anhydride are dissolved in 50 ml water and the solution evaporated to dryness. The resultant acid is characterized by NMR.

NMR in D$_2$O.

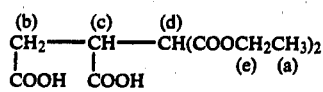

(a) CH$_3$ triplet centered at 1.25δ
(b) CH$_2$ ABX doublet at 2.65–2.95δ
(c) CH ABX multiplet at 3.40–3.80δ
(d) CH doublet centered at 4.0δ
(e) CH$_2$ quartet centered at 4.16δ
DHO at 4.74δ.

EXAMPLE 6

PREPARATION OF α-(DIETHYLMALONYL)SUCCINIC ACID 80 grams (0.82 mole) malonic anhydride, 230 grams (1.4 moles) diethyl malonate and 10 grams (0.23 mole) sodium acetate are combined, stirred for 1 hour and allowed to stand overnight. 224 grams of 12% hydrochloric acid are added and the solution is evaporated down to a syrup. The syrup is dissolved in 600 ml water and extracted with carbon tetrachloride until the CCl$_4$ fraction contains no diethyl malonate. 160.6 grams (73.3% yield) of acid product are obtained.

EXAMPLE 7

PREPARATION OF α-(ACETYL CARBOMETHOXY METHINYL)SUCCINIC ACID 20 grams (0.2 mole) maleic anhydride are dissolved in 100 grams (0.86 mole) methyl acetoacetate. Five grams (0.06 mole) sodium acetate are added slowly, the temperature rising to 95° C. The solution is stirred for eight hours. 306 grams 2% hydrochloric acid are added and the water and excess acetoacetate are removed under vacuum. The residue is dissolved in acetone, the solution filtered, and evaporated. The residue is dissolved in 200 ml water and excess acetoacetate is removed by extraction with carbon tetrachloride. 31 grams of acid are obtained and characterized.

NMR in D$_2$O

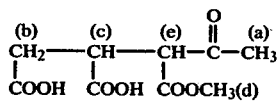

(a) CH$_3$ singlet at 1.82δ
(b) CH$_2$ ABX multiplet at 2.72–3.20δ
(c) CH ABX multiplet at 3.40–3.90δ
(d) CH$_3$ singlet at 3.96δ
(e) CH hidden under CH$_3$'s
DHO at 4.86δ.

The NMR also shows evidence of the formation of another compound, probably of the formula

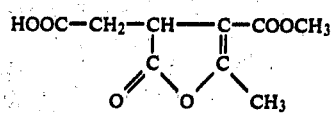

EXAMPLE 8

PREPARATION OF α-(CYANO CARBOMETHOXY METHINYL)SUCCINIC ACID 20 grams (0.2 moles) maleic anhydride are dissolved in 90 grams (0.91 moles) methyl cyanoacetate. Five grams (0.06 mole) sodium acetate are added and the solution is stirred for eight hours. 206 grams, 3% hydrochloric acid are added and the solution extracted with carbon tetrachloride until the CCl$_4$ contains no trace of cyanoacetate. The water solution is evaporated to dryness, the residue is dissolved in acetone, and the solution filtered. The acetone solution is evaporated and 0.47 grams of product obtained.

NMR in D$_2$O

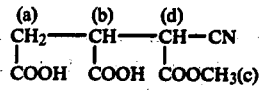

(a) CH$_2$ ABX multiplet at 2.24–2.91δ
(b) CH ABX multiplet at 3.15–3.49δ
(c) CH$_3$ singlet at 3.58δ
(d) hidden

EXAMPLE 9

PREPARATION OF α-(DIETHYL METHYL MALONYL)SUCCINIC ACID 20 grams (0.2 moles) maleic anhydride are dissolved in 80 grams (0.46 mole) diethyl methyl malonate. 7.5 grams (0.087 mole) sodium acetate are added, and the solution is heated to 60°–70° C. for 3–4 hours, then allowed to stand overnight. 209 grams 4.6% NCl is added, and the solution is evaporated. The residue is dissolved in acetone, filtered and evaporated to dryness. The residue is dissolved in 300 ml water, and extracted with CCl$_4$ to remove unreacted diethyl methyl malonate. The water solution is evaporated to obtain 39.2 grams of product (67% yield).

NMR in CDCl$_3$

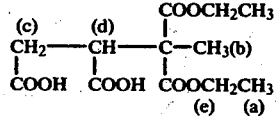

(a) CH$_3$ triplet centered at 1.58δ
(b) CH$_3$ singlet at 1.53δ
(c) CH$_2$ ABX multiplet at 2.6–3.04δ
(d) CH ABX multiplet at 3.60–3.95δ
(e) CH$_2$ quartet centered at 4.25δ

EXAMPLE 10

PREPARATION OF α-(1-NITROETHYL)SUCCINIC ACID 20 grams maleic anhydride are dissolved in 75 grams (1 mole) nitroethane. 7.5 grams (0.086 mole) sodium acetate are added and the solution is refluxed for 7 hours at about 115° C. 209 grams 4.6% HCl are added and the solution is evaporated down. The residue is dissolved in acetone and filtered and the filtrate is evaporated down. A mixture of product and maleic acid is obtained.

NMR in D₂O $$\underset{COOH}{\underset{|}{\overset{(b)}{CH_2}}}-\underset{COOH}{\underset{|}{\overset{(c)}{CH}}}-\underset{CH_3(a)}{\underset{|}{\overset{(d)}{CH}}}-NO_2$$

(a) CH₃ doublet centered at 2.04δ
(b) (c) CH₂, CH at 3.2–3.6δ
(d) CH doublet of doublets at 5.13δ

EXAMPLE 11

PREPARATION OF α-(DIMETHYL TARTRONYL)SUCCINIC ANHYDRIDE 9.9 grams (0.1 mole) of maleic anhydride and 2 grams sodium acetate are dissolved in 15 grams (0.1 mole) dimethyl tartronate. The solution is heated to 100° C. for one-half hour, then to 125° C. for another one-half hour. A sample is removed for NMR analysis. The reaction mixture is retained for use in Example 12.

NMR in CDCl₃

(a) CH₂ ABX multiplet at 2.60–3.02δ
(b) CH₃ singlet at 3.91δ
(c) hidden beneath CH₃'s

EXAMPLE 12

PREPARATION OF ISOCITRIC/ALLOISOCITRIC ACID AND THEIR LACTONES

To the remaining reaction mixture of Example 11 is added 340 grams of 12% HCl, and the solution is refluxed for 3 hours. The solution is then evaporated to dryness and the residue extracted with 200 ml acetone and filtered. The acetone is evaporated and 16.8 grams of product are recovered.

EXAMPLE 13

PREPARATION OF α-(DIMETHYLCHLOROMALONYL)SUCCINIC ACID 24.8 grams (0.1 mole) of α-(dimethylmalonyl)succinic acid prepared as in Example 1 are dissolved in 200 ml water. 30 grams 5.2% sodium hypochlorite solution are added slowly to a pH of 5.4, and the solution is acidified to pH 2.0. The solution is then evaporated to dryness, and the residue dissolved in 200 ml acetone, and that solution filtered. The acetone solution is evaporated down to produce 23 grams of product (82% yield).

NMR in D₂O $$\underset{COOH}{\underset{|}{CH_2}}-\underset{COOH}{\underset{|}{CH}}-\underset{COOCH_3(b)}{\underset{|}{\overset{COOCH_3(b)}{|}C}}-Cl$$

(a) CH₂ ABX doublet at 2.90–3.15δ

(b) CH₃ singlet at 4.04δ
(c) ABX triplet at 4.1–4.39δ
DHO at 4.71δ

EXAMPLE 14

PREPARATION OF α-(DIMETHYL HYDROXYMALONYL)SUCCINIC ACID GAMMA LACTONE 24.8 grams (0.1 mole) of α-(dimethylmalonyl)succinic acid produced as in Example 1, is dissolved in 200 ml water. 300 grams 5% sodium hypochlorite solution are added slowly at a pH of 5.4. The reaction mixture is stirred for 15 minutes and 10 grams sodium carbonate are added to a pH of 8.6–9.0. The solution is stirred at 80°–85° C. for one-half hour, cooled and acidified with 10% HCl to a pH of 1.0. The solution is then evaporated, and the residue dissolved in acetone and filtered. 17 grams of product are obtained by evaporating the acetone.

NMR in D₂O (a) CH₂ ABX multiplet at 2.70–3.01δ
(b) CH₃ singlet at 3.72δ
(c) CH ABX multiplet at 3.75–4.04δ
DHO at 4.63δ

EXAMPLE 15

PREPARATION OF α-(DIMETHYL CHLOROMALONYL)SUCCINIC ACID 27.6 grams (0.1 mole) of diethyl malonyl succinic acid as prepared in Example 5 are dissolved in 200 ml water. 400 ml 5% sodium hypochlorite solution is added slowly to pH 5.3 and the solution is stirred for ½ hour. 10% HCl is added to pH 1.3 and the solution evaporated to dryness. The residue is dissolved in 200 ml acetone, and the solution filtered and evaporated. 29 grams (94% yield) of product are obtained.

NMR in D₂O $$\underset{COOH}{\underset{|}{\overset{(b)}{CH_2}}}-\underset{COOH}{\underset{|}{\overset{(c)}{CH}}}-\underset{COOCH_2CH_3}{\underset{|}{\overset{COOCH_2CH_3}{|}C}}-Cl \;\; (d)\;(a)$$

(a) CH₃ triplet centered at 1.27δ
(b) CH₂ ABX multiplet at 2.71δ
(c) CH ABX multiplet at 4.05–4.29δ
(d) CH₂ quartet centered at 4.40δ
DHO at 4.75δ

EXAMPLE 16

PREPARATION OF α-(DIETHYL BROMOMALONYL)SUCCINIC ACID 27.6 grams (0.1 mole) of α-(diethyl malonyl)succinic acid as prepared in Example 5 are dissolved in 200 ml water. 10 g Na₂CO₃ are added to a pH of 5.0 and 27 grams of bromine are added slowly, while the pH is maintained at 4.0–4.5 with additional Na₂CO₃. After stirring for ½ hour, the solution is acidified to pH 1.3 with 10% HCl, and evaporated to dryness. The residue is dissolved in acetone and the solution is filtered and evaporated in vacuo to give 30 grams of product containing some unreacted product of Example 3.

NMR in D₂O

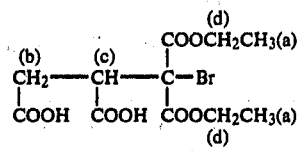

(a) CH₃ triplet centered at 1.32δ
(b) CH₂ ABX multiplet at 3–3.23δ
(c) CH hidden
(d) CH₂ two quartets; one centered at 4.40δ, one at 4.46δ
DHO at 4.82δ

EXAMPLE 17

PREPARATION OF α-(2-HYDROXY DISODIUM MALONYL)DISODIUM SUCCINATE 9.4 grams (0.03 mole) of α-(di-ethyl chloro malonyl)-succinic acid, as prepared in Example 15, is mixed with 75 ml water and 4.4 g (0.06 mole) of Ca(OH)₂. After 15 minutes an additional 3 grams of Ca(OH)₂ is added to maintain the pH at 9.5–10.0. The resulting mixture is heated at 60°–70° C. for 4 hours while stirring and maintaining the pH at 9.5–10.0 by further addition of Ca(OH)₂ as required. Sodium carbonate, 0.1 mole, is then added and the reaction mixture is stirred at 60°–70° C. for 15 minutes. The solution is filtered to remove CaCO₃ and the pH of the filtrate is adjusted to 9.0 with dilute hydrochloric acid. After evaporation of the water, a residue of the α-(2-hydroxy disodium malonyl)-disodium succinate containing traces of sodium chloride is obtained. The structure of the product is confirmed by NMR analysis (D₂O):

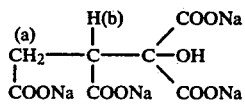

(a) CH₂ 2.25–2.7δ
(b) H 3.0–3.9δ

EXAMPLE 18

PREPARATION OF ISOCITRIC AND ALLOISOCITRIC ACID LACTONES

Procedure A

One gram of the product prepared in Example 17 above is acidified with dilute HCl (10% (with liberation of CO₂) and evaporated to dryness in vacuo. The product consists of a mixture of isocitric and alloisocitric acid lactones by NMR analysis (D₂O):

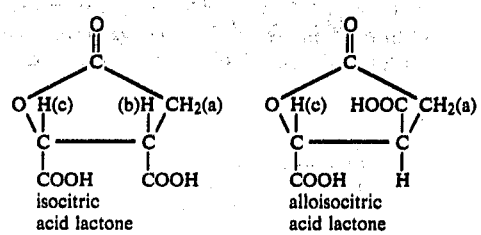

(a) CH₂ ABX multiplet at 2.94–3.28δ
(b) H ABX multiplet at 3.78–4.19δ
(c) H doublet at 5.38–5.58δ
(c') H doublet at 4.3–4.5δ (traces of isocitric acid and alloisocitric acid)

Procedure B

Fifty grams of the compound prepared in Example 17, i.e. the sodium salt of α-(diethyl chloromalonyl)succinate is dissolved in 100 ml of water to which 10 ml of concentrated hydrochloric acid has been added. The solution is refluxed for 16 hours and then evaporated in vacuo to leave a solid residue consisting of a 1:1 mixture of the lactones of isocitric acid and alloisocitric acid (structure determined by NMR analysis—D₂O).

EXAMPLE 19

PREPARATION OF TETRASODIUM PROPENE 1,1,2,3-TETRACARBOXYLATE 10 grams (0.036 moles) of α-(dimethyl chloromalonyl)succinic acid, as prepared in Example 15, is mixed with 200 ml water. Ca(OH)₂ is then slowly added at first maintaining the pH at 10.0 and then heating to 60°–70° C. until all the ester groups are saponified. A total of 10 grams of Ca(OH)₂ is added (pH 11.6) and the slurry is stirred for 2–3 hours at 60°–70° C. Thirteen grams of Na₂CO₃ is then added and the mixture is stirred for 15 minutes at 50° C. The precipitated CaCO₃ is filtered and the filtrate is evaporated to give the tetrasodium propene 1,1,2,3-tetracarboxylate. The structure is confirmed by NMR analysis (D₂O): —CH₂—(a) singlet at 3.34δ.

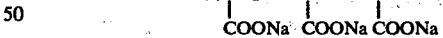

EXAMPLE 20

PREPARATION OF 1:1 CIS:TRANS ACONITIC ACID

Nine grams of the product as prepared in Example 19, i.e. tetrasodium propene-1,1,2,3-tetracarboxylate, is dissolved in 100 mls water and acidified with dilute HCl (10%). Liberation of CO₂ is instantaneous. The residue, after evaporation of water, is extracted with acetone. The acetone is evaporated to leave a residue consisting of a 1:1 by weight mixture of cis:trans aconitic acid. The structure of the product is confirmed by NMR analysis (D₂O):

cis Aconitic Acid

-continued

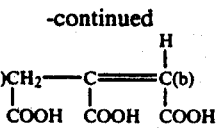

(a) CH₂ singlet at 3.44δ
(b) CH singlet at 6.33δ trans Aconitic Acid

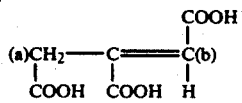

(a) CH₂ singlet at 3.80δ
(b) CH singlet at 3.92δ

EXAMPLE 21

PREPARATION OF ISOCITRIC ACID, ALLOISOCITRIC ACID AND THEIR LACTONES 28 grams (0.1 mole) of α-(dimethyl chloromalonyl)-succinic acid, as prepared in Example 15 is mixed with 200 ml water. Sodium hydroxide, 20 g (0.05 mole), is added slowly while maintaining the temperature at 60° C. and the pH between 9 and 10. After heating for 3–4 hours at 60° C., the solution is cooled and acidified to a pH of 1.2 with dilute hydrochloric acid. The heated solution is then evaporated in vacuo and the residue remaining is extracted with acetone. The acetone extract is then filtered and the filtrate, evaporated to give a residue of a mixture of 1:1 isocitric acid:alloisocitric acid and the lactones thereof (identified by NMR).

EXAMPLE 22

PREPARATION OF ISOCITRIC ACID, ALLOISOCITRIC ACID AND THEIR LACTONES 15.6 grams (0.05 mole) of α-(diethyl chloromalonyl)-succinic acid as prepared in Example 15 is mixed with 200 ml water. 25 grams (0.43 mole) magnesium hydroxide is added slowly while maintaining the reaction mixture at 80°–90° C. and the pH at 9.0. After refluxing the reaction mixture for 2 hours, the solution is cooled and then acidified with 86.2 g of 50% sulfuric acid. The acidified solution is evaporated to yield a residue which is then extracted with acetone. The acetone extract is filtered and the filtrate evaporated to give a residue consisting of a mixture of isocitric acid and alloisocitric acid and the lactones thereof (identified by NMR).

This invention has been described with respect to certain preferred embodiments and various modifications and variations in the light thereof will be suggested to persons skilled in the art and are to be included within the spirit and purview of this application and the scope of the appended claims.

What is claimed is:

1. A polyfunctional compound of the formula

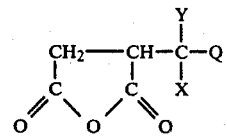

wherein
(A) X is COOR and R is methyl or ethyl;
(B) Y is CN or COCH₃, and
(C) Q is H.

2. A compound as defined in claim 1 wherein said X is COOCH₃, Y is COCH₃ and Q is H.

3. A compound as defined in claim 1 wherein said Q is H, Y is CN and X is COOCH₃.

4. A polyfunctional compound of the formula

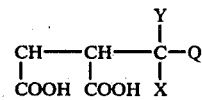

wherein
(A) X is COOR and R is methyl or ethyl;
(B) Y is CN or COCH₃, and
(C) Q is H.

* * * * *

UNITED STATES PATENT AND TRADEMARK OFFICE
CERTIFICATE OF CORRECTION

PATENT NO. : 4,272,442
DATED : June 9, 1981
INVENTOR(S) : Gutierrez, Eddie N.

It is certified that error appears in the above-identified patent and that said Letters Patent are hereby corrected as shown below:

Column 12, line 42: change "NCl" to --HCl--.

Column 12, line 57: change "1.58δ to --1.38δ--.

Column 11, line 26: change "malonic anhydride" to --maleic anhydride--.

Column 13, lines 62-66:

Change
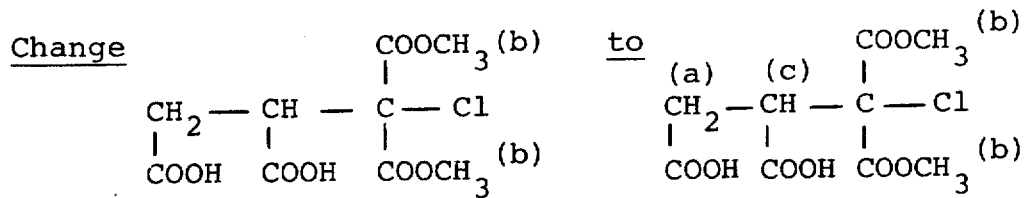

UNITED STATES PATENT AND TRADEMARK OFFICE
CERTIFICATE OF CORRECTION

PATENT NO. : 4,272,442

DATED : June 9, 1981

INVENTOR(S) : Gutierrez et al

It is certified that error appears in the above-identified patent and that said Letters Patent are hereby corrected as shown below:

Column 16, lines 47-52:

Change: 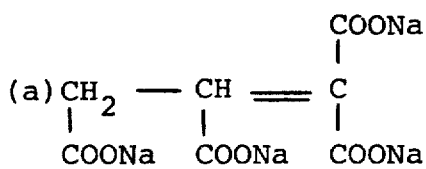 To 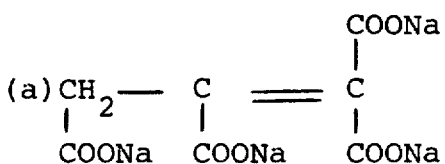

Column 17, line 16: change "3.92δ" to --6.92δ--.

Signed and Sealed this

Tenth Day of November 1981

[SEAL]

Attest:

GERALD J. MOSSINGHOFF

Attesting Officer

Commissioner of Patents and Trademarks